United States Patent [19]

Mayer et al.

[11] 4,110,334

[45] Aug. 29, 1978

[54] DERIVATIVES OF 1-OXA-3,8-DIAZA-SPIRO-[4,5]-DECANES

[75] Inventors: Norbert Mayer, Gersthofen; Gerhard Pfahler, Augsburg; Hartmut Wiezer, Gersthofen, all of Germany

[73] Assignee: Hoechst Aktiengesellschaft, Frankfurt am Main, Germany

[21] Appl. No.: 766,948

[22] Filed: Feb. 9, 1977

[30] Foreign Application Priority Data

Feb. 14, 1976 [DE] Fed. Rep. of Germany ....... 2606026

[51] Int. Cl.$^2$ .................... C07D 498/10; C07D 498/20
[52] U.S. Cl. ........................ 260/293.66; 260/293.63; 260/293.64; 260/45.8 NZ; 260/45.8 N
[58] Field of Search ...................... 260/293.63, 293.64, 260/293.66, 45.8 NZ, 45.8 N

[56] References Cited

U.S. PATENT DOCUMENTS

| | | | |
|---|---|---|---|
| 3,534,048 | 10/1970 | Murayama et al. | 260/293.63 |
| 3,941,744 | 3/1976 | Murayama et al. | 260/45.8 NZ |

FOREIGN PATENT DOCUMENTS

| | | | |
|---|---|---|---|
| 1,541,715 | 9/1968 | France | 260/293.66 |
| 1,227,965 | 4/1971 | United Kingdom | 260/293.66 |

*Primary Examiner*—Natalie Trousof
*Assistant Examiner*—Robert T. Bond
*Attorney, Agent, or Firm*—Connolly and Hutz

[57] ABSTRACT

Derivatives of 1-oxa-3,8-diaza-spiro-[4,5]-decane, which be prepared by reacting a 2,2-dimethyl-6,6-dialkyl-4-hydroxy-4-carbamoylpiperidine with an aldehyde or ketone, are excellently suitable as light stabilizers for organic materials.

6 Claims, No Drawings

DERIVATIVES OF 1-OXA-3,8-DIAZA-SPIRO-[4,5]-DECANES

It is known that the properties of organic polymers are affected detri-mentally by the action of light, especially by long-wave ultraviolet. This action results in modifications of the color of the polymers (yellowing) or in deteriorations of their physical properties, for example a reduction of the tensile strength or a tendency to get brittle etc.

It has now been found that the 7,7-dimethyl-9,9-dialkyl-1-oxa-3,8-diaza-4-oxo-spiro-[4,5]-decanes which have not been disclosed hitherto, as well as their salts, provided that said decanes are capable of forming salts, are excellently appropriate as light stabilizers for organic materials.

The present invention consequently relates to the aforesaid derivatives of 1-oxa-3,8-diaza-spiro-[4,5]-decanes, to a process for their preparation and to their application as stabilizers for organic polymers against the decomposing action of light, especially of ultraviolet light which results in a discoloration and/or brittleness of the polymers.

The novel compounds correspond to the formula

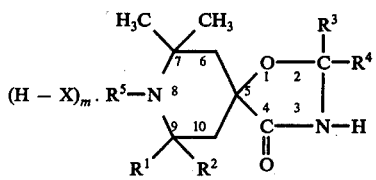

wherein $R^1$ and $R^2$ each mean identical or different straight chain or branched alkyl radicals having of from 1 to 12 carbon atoms or $R^1$ and $R^2$ mean together with the attached carbon atom an optionally methyl-substituted cyclopentyl or cyclohexyl ring or a grouping of the formula

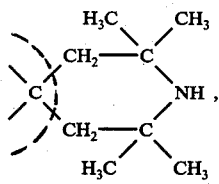

$R^3$ and $R^4$ which are identical or different, mean hydrogen alkyl or isoalkyl groups having of from 1 to 30 carbon atoms or aryl radicals having of from 6 or 10 carbon atoms which may be substituted by halogen or an alkyl radical having of from 1 to 4 carbon atoms, or aralkyl radicals having of from 7 to 10 carbon atoms, or $R^3$ and $R^4$ mean together with the attached carbon atom a cycloalkyl group having of from 4 to 15 carbon atoms, which may be substituted by a $C_1$-$C_4$ alkyl group, or a grouping of the formula

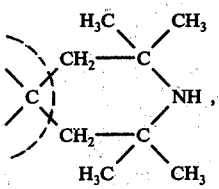

$R^5$ means a hydrogen atom, an oxygen atom or a hydroxyl group or an alkyl group having of from 1 to 4 carbon atoms, H—X means phosphoric acid, phosphorous acid, an aliphatic or aromatic sulfonic acid or phosphonic acid, aliphatic mono-, di- or polycarboxylic acid or an aromatic mono- or dicarboxylic acid and $m$ is 0 or 1 and, when $>$N—$R^5$ is not basic, always 0.

Repretatives of the 7,7-dimethyl-9,9-dialkyl-1-oxa-3,8-diaza-4-oxo-spiro-[4,5]-decanes are, for example 2-iso-propyl-7,7,9,9-tetramethyl-1-oxa-3,8-diaza-4-oxo-spiro-[4,5]decane
2-butyl-7,7,9,9-tetramethyl-1-oxa-3,8-diaza-4-oxo-spiro-[4,5]decane
2-iso-butyl-7,7,9,9-tetramethyl-1-oxa-3,8-diaza-4-oxo-spiro-[4,5]-decane
2-pentyl-7,7,9,9-tetramethyl-1-oxa-3,8-diaza-4-oxo-spiro-[4,5]-decane
2-iso-pentyl-7,7,9,9-tetramethyl-1-oxa-3,8-diaza-4-oxo-spiro-[4,5]-decane
2-hexyl-7,7,9,9-tetramethyl-1-oxa-3,8-diaza-4-oxo-spiro-[4,5]-decane
2-heptyl-7,7,9,9-tetramethyl-1-oxa-3,8-diaza-4-oxo-spiro-[4,5]-decane
2-iso-heptyl-7,7,9,9-tetramethyl-1-oxa-3,8-diaza-4-oxo-spiro-[4,5]-decane
2-iso-octyl-7,7,9,9-tetramethyl-1-oxa-3,8-diaza-4-oxo-spiro-[4,5]-decane
2-nonyl-7,7,9,9-tetramethyl-1-oxa-3,8-diaza-4-oxo-spiro-[4,5]-decane
2-iso-nonyl-7,7,9,9-tetramethyl-1-oxa-3,8-diaza-4-oxo-spiro-[4,5]-decane
2-undecyl-7,7,9,9-tetramethyl-1-oxa-3,8-diaza-4-oxo-spiro-[4,5]-decane
2-phenyl-7,7,9,9-tetramethyl-1-oxa-3,8-diaza-4-oxo-spiro-[4,5]-decane
2-(4-chloro-phenyl)-7,7,9,9-tetramethyl-1-oxa-3,8-diaza-4-oxo-spiro-[4,5]-decane
2,2-dimethyl-7,7,9,9-tetramethyl-1-oxa-3,8-diaza-4-oxo-spiro-[4,5]-decane
2-ethyl-2,7,7,9,9-pentamethyl-1-oxa-3,8-diaza-4-oxo-spiro-[4,5]-decane
2-propyl-2,7,7,9,9-pentamethyl-1-oxa-3,8-diaza-4-oxo-spiro-[4,5]-decane
2-iso-propyl-2,7,7,9,9-pentamethyl-1-oxa-3,8-diaza-4-oxo-spiro-[4,5]-decane
2-butyl-2,7,7,9,9-pentamethyl-1-oxa-3,8-diaza-4-oxo-spiro-[4,5]-decane
2-iso-butyl-2,7,7,9,9-pentamethyl-1-oxa-3,8-diaza-4-oxo-spiro-[4,5]-decane
2-pentyl-2,7,7,9,9-pentamethyl-1-oxa-3,8-diaza-4-oxo-spiro-[4,5]-decane
2-hexyl-2,7,7,9,9-pentamethyl-1-oxa-3,8-diaza-4-oxo-spiro-[4,5]-decane
2-nonyl-2,7,7,9,9-pentamethyl-1-oxa-3,8-diaza-4-oxo-spiro-[4,5]-decane
2,2-diethyl-7,7,9,9-tetramethyl-1-oxa-3,8-diaza-4-oxo-spiro-[4,5]-decane
2,2-dipropyl-7,7,9,9-tetramethyl-1-oxa-3,8-diaza-4-oxo-spiro-[4,5]-decane
2,2-dibutyl-7,7,9,9-tetramethyl-1-oxa-3,8-diaza-4-oxo-spiro-[4,5]-decane
2-ethyl-2-pentyl-7,7,9,9-tetramethyl-1-oxa-3,8-diaza-4-oxo-spiro-[4,5]-decane
2,2-dibenzyl-7,7,9,9-tetramethyl-1-oxa-3,8-diaza-4-oxo-spiro-[4,5]-decane
2,2,4,4-tetramethyl-7-oxa-3,12-diaza-14-oxo-dispiro-[5,1,4,2]-tetradecane 2,2,4,4-tetramethyl-7-oxa-3,20-diaza-21-oxo-dispiro-[5,1,11,2]-heneicosane 2,2,4,4-tetramethyl-7-oxa-3,14-diaza-15-oxo-dispiro-[5,5,5,2]-pentadecane 2,2,4,4,10,10,12,12-octamethyl-7-oxa-3,11,14-triaza-15-oxo-dispiro-[5,1,5,2]-pentadecane 2-ethyl-2,7,7,9,9-pentamethyl-1-oxa-3,8-diaza-4-oxo-8-oxyl-spiro-[4,5]-decane The compounds according to the invention wherein $m$ is 0 and $R^5$ is H are obtained by reacting a 2,2-dimethyl-6,6-dialkyl-4-hydroxy-4-carbamoylpiperidine of the formula

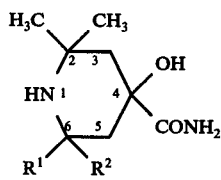

wherein $R^1$ and $R^2$ are defined as above, or a salt of said piperidine, preferably a hydrochloride with an aldehyde or a ketone of the formula

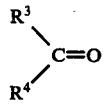

wherein $R^3$ and $R^4$ are defined as above. The reaction is carried out in an organic solvent, preferably glacial acetic acid using a dehydrating agent, for example sulfuric acid or poly - phosphoric acid, preferably sulfuric acid, at a temperature of from 0° C. to 180° C., preferably of from 20° C. to 120° C. and, when using aldehydes, especially of from 20° C. to 30° C. When using glacial acetic acid as solvent, the procedure is as follows:

the 5- to 10-fold quantity of glacial acetic acid, calculated on carbamoyl-piperidine, is added to 1 mol of hydroxycarbamoylpiperidine and to 1 to 3 mols of the carbonyl compound and 2 mols of concentrated, sulfuric acid are added dropwise. The sulfates of the compounds of the invention generally precipitate in the course of the reaction, if they don't, the reaction mixture must be concentrated. The free bases are obtained from the salts by treating the latter with ammonia or with alkali hydroxide solutions. Salts of organic or mineral acids may be prepared from the free bases, preferably in the presence of a solvent or of water. Compounds wherein $R^5$ is an alkyl radical are obtained by reacting the compounds wherein $R^5$ is hydrogen by alkylation with alkyl halides, preferably with bromides and iodides. The compounds wherein $R^5$ is =O or —OH may be prepared from compounds wherein $R^5$ is H, for example by a treatment with hydrogen peroxide.

A preferred 4-hydroxy-4-carbamoylpiperidine is 2,2,6,6-tetramethyl-4-hydroxy-4-carbamoylpiperidine; suitable aldehydes or ketones are, for example formaldehyde, isobutyraldehyde, n-valeraldehyde, isovaleraldehyde, caproaldehyde, 2-ethylbutyraldehyde, enanthaldehyde, 2-ethylcaproaldehyde, isononyl aldehyde, capric aldehyde, isodecyl aldehyde, lauric aldehyde, benzaldehyde, p-chlorobenzaldehyde, acetone, methyl ethyl ketone, methyl propyl ketone, methyl isopropyl ketone, hexanone-2, methyl isobutyl ketone, hetanone-2, octanone-2, undecanone-2, diethyl ketone, heptanone-4, nonanone-5, octanone-3, dibenzyl ketone, cyclopentanone, cyclohexanone, cyclododecanone, benzophenone and 2,2,6,6-tetramethylpiperidine-4-one (=triacetonamine).

In the novel compounds of the formula

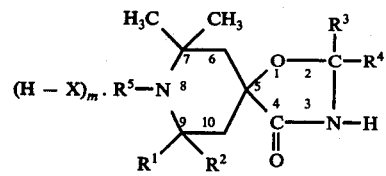

the radicals $R^1$ and $R^2$ which may be identical or different, each mean straight chain or branched alkyl radicals having from 1 to 12, preferably of from 1 to 6 carbon atoms. Compounds derived from the readily accessible triacetone-amine are especially important. In this case $R^1$ and $R^2$ are methyl groups. $R^1$ and $R^2$ may form, together with the attached carbon atom, a cyclopentane or a cyclohexane ring which may be substituted by a methyl group, or a grouping of the formula

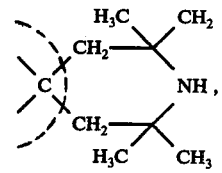

$R^1$ and $R^2$ each may stand for methyl, isobutyl, hexyl and $R^1$ and $R^2$, together with the attached carbon atom, may stand for cyclohexyl, cyclopentyl and 2,2,6,6-tetramethylpiperidyl.

The radicals $R^3$ and $R^4$ are derived from the aldehydes or ketones used in the synthesis of the compounds of the invention. They may be identical or different. $R^3$ and $R^4$ are, consequently, hydrogen or alkyl or isoalkyl radicals having of from 1 to 30 carbon atoms or aryl radicals having of from 6 to 10 carbon atoms which may be substituted by halogen, preferably chlorine or an alkyl radical having of from 1 to 4 carbon atoms, or aralkyl radicals having of from 7 to 10 carbon atoms, the aliphatic chain having of from 1 to 4 carbon atoms.

The meanings of $R^3$ and $R^4$ depend on the compounds from which they derive.

If they derive from an aldehyde, $R^3$ is necessarily always hydrogen, whereas $R^4$ is hydrogen, an alkyl radical having of from 1 to 30, preferably of from 1 to 18 and especially of from 3 to 12 carbon atoms or an aryl radical having of from 6 to 10 carbon atoms (phenyl or naphthyl) which may be substituted by a halogen atom, preferably chlorine, or an alkyl radical having of from 1 to 4 carbon atoms or an aralkyl radical having of from 7 to 10 carbon atoms, of from 1 to 4 carbon atoms belonging to the aliphatic chain.

If the novel compounds have been synthesized from 4-hydroxy-4-carbamoylpiperidines and from ketones, $R^3$ means preferably an alkyl group having of from 1 to 30, preferably 1 to 7 and especially 1 to 4, carbon atoms or an aralkyl radical having of from 7 to 10 carbon atoms, the aliphatic chain having of from 1 to 4 carbon atoms. $R^4$ means in this case an alkyl radical having of from 1 to 30, preferably of from 1 to 17 and especially of from 1 to 10, carbon atoms or an aryl radical having of from 6 to 10 carbon atoms which may be substituted by a halogen atom, preferably chlorine, or an alkyl radical having of from 1 to 4 carbon atoms, or an aralkyl radical having of from 7 to 10 carbon atoms, the aliphatic chain having of from 1 to 4 carbon atoms.

$R^3$ may have the following meanings: methyl, ethyl, propyl, isopropyl, butyl, isobutyl, pentyl, isopentyl, hexyl, isohexyl, heptyl, octyl, isooctyl, nonyl, isononyl, decyl, undecyl, dodecyl, tridecyl, tetradecyl, pentadecyl, heptadecyl, 4-isopropyl-phenyl, 2-ethyl-butyl, 2-ethyl-hexyl, 4-methyl-benzyl, phenyl, 2-chlorophenyl, 3-chlorophenyl, 4-chlorophenyl, 1-naphthyl, 2-naphthyl, benzyl, 2-methyldecyl, $R^4$ may represent methyl, ethyl, propyl, isopropyl, butyl, isobutyl, pentyl, isopentyl, hexyl, heptyl, octyl, nonyl, decyl, undecyl, pentadecyl, heptadecyl, phenylethyl, benzyl and phenyl.

$R^3$ and $R^4$ finally may mean, together with the attached carbon atom, a cycloalkyl group having of from 4 to 15, preferably of from 5 to 12 and especially of from 5 to 7, carbon atoms. The cycloalkyl group may be substituted by a $C_1$–$C_4$ alkyl group. $R^3$ and $R^4$ together may moreover mean the cyclic group of the formula

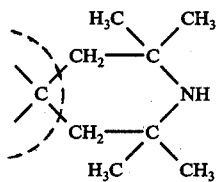

Examples of said group are cyclopentyl, 3-methylcyclopentyl, cyclohexyl, 2-methyl cyclohexyl, 3-methylcyclohexyl, 4-methylcyclohexyl, cycloheptyl, cyclooctyl, cyclononyl, cyclodecyl, cycloundecyl, cyclododecyl, cyclotridecyl, cyclopentadecyl, and 2,2,6,6-tetramethylpiperidyl.

$R^5$ is preferably hydrogen. It may moreover be oxygen or a hydroxy group or an alkyl group having of from 1 to 4 carbon atoms.

H—X means phosphoric acid, phosphorous acid, an aliphatic sulfonic acid or phosphonic acid having of from 1 to 30, preferably of from 1 to 18, carbon atoms, an optionally alkylated aromatic sulfonic or phosphonic acid having of from 6 to 25, preferably of from 6 to 18, carbon atoms, of from 1 to 3 alkyl groups having of from 1 to 16 carbon atoms being optionally present. H—X may further have the meaning of an aliphatic, straight chain or branched mono- or dicarboxylic acid having of from 2 to 34, preferably of from 2 to 18 carbon atoms or optionally a polycarboxylic acid having up to 4 carboxyl groups and a total of up to 16 carbon atoms, or an aromatic mono- or dicarboxylic acid having of from 7 to 25, preferably of from 7 to 19, carbon atoms which may be substituted by $C_1$–$C_4$ alkyl or isoalkyl groups. Examples of possible meanings of H—X are phenylphosphonic acid, camphorsulfonic acid, dodecylsulfonic acid, p-toluenesulfonic acid, alkyl polyglycol ether sulfonic acid, alkylaryl polyglycol ether sulfonic acids, acetic acid, propionic acid, n-octanoic acid, 2-ethylhexanoic acid, lauric acid, stearic acid, tallow fatty acid, montanoic acid, succinic acid, adipic acid, azelaic acid, citric acid, tricarballylic acid, benzoic acid, tolylic acid, p-tert.-butylbenzoic acid, phthalic acid, and terephthalic acid.

In the general formula, "m" indicates that the invention relates both to the free bases and to the aforesaid salts, or, in the case of polybasic acids, likewise to acid salts of 1-oxa-3,8-diaza-spiro-[4,5]-decanes, "m" being consequently 0 or 1. In compounds wherein the group >N—$R^5$ is not capable of forming salts "m" is necessarily 0.

The 1-oxa-3,8-diaza-spiro-[4,5]-decanes confer upon organic polymer compositions an excellent stability against the decomposition by the action of heat and especially of ultraviolet radiation. They are especially important as light stabilizers for polyolefins. The color properties of the organic polymer compositions are not affected detrimentally by the novel compounds.

Organic polymer compositions which shall be protected against the detrimental action of light and heat comprise in this context, for example, polyolefins, such as polyisoprene, polybutadiene, polystyrene and especially polypropylene and polyethylene of low and of high density, moreover ethylenepropylene copolymers, ethylene-butene copolymers, ethylenevinyl acetate copolymers, styrene-butadiene copolymers and acrylonitrile-styrene-butadiene copolymers.

The terms "polyvinyl chloride" and "polyvinylidene chloride" should be understood to mean homopolymers of vinyl chloride and vinylidene chloride, copolymers of vinyl chloride or vinylidene chloride with vinyl acetate or other olefinically unsaturated monomers. Polyacetals, polyesters, for example polyethylene terephthalte, polyamides, for example nylon-6, nylon-6,6, nylon-6,10, polyurethanes and epoxy resins are also suitable.

The novel compounds are furthermore suitable for the stabilization of animal and vegetable oils and fats, for example lin seed oil, peanut oil, ricinus oil, fat, lard, and the like, liquid and solid hydrocarbons such as gasoline mineral oil, wax, resins and the like.

The quantity of the novel compounds to be added to the synthetic polymers depends on the nature, the properties and the special application purposes of the organic polymer to be stabilized and may vary considerably. In general, of from 0.01 to 5 parts by weight, preferably of from 0.05 to 3 parts by weight, especially of from 0.1 to 1.5 parts by weight, calculated on the quantity of the synthetic polymer are used. A single compound may be used as well as a mixture of compounds.

The compounds according to the invention are incorporated into the organic polymers by usual methods, for example by mixing in the form of powders, or by introducing a solution, suspension or emulsion of the stabilizer into a solution, suspension or emulsion of the organic polymer.

The stabilizers are effective both when used solely and when used in admixture with conventional light and heat stabilizers based on phenolic, sulfidic and phosphor-containing antioxidants.

As conventional stabilizers there may be mentioned, by way of example, 2,6-di-tert-butyl-p-kresol, 3,5-di-tert-butyl-4-hydroxy-phenylpropionic acid ester, alkylidene-bis-alkylphenols, thiodipropionic acid esters of fatty alcohols as well as dioctadecylsulfide and -disulfide. Suitable phosphorus-containing compounds are for example trisnonylphenyl phosphite, disstearylpentaerythrityl diphosphite, ester of pentaerylthritol phosphite and others. Examples of UV adsorbers are the benzotriazoles such as 2-(2'-hydroxy-5'-methylphenyl)-benzotriazole, examples of quenchers are piperidine stabilizers and metal chelates.

An addition of the novel stabilizers in the stabilization of the previously described chlorine-containing homo- and copolymers as well as of chlorinated polyolefins, for example chlorinated polyethylene and polypropylene, in the presence of metal compounds known as stabilizers, of epoxy resins, phosphites and optionally polyhydric alcohols likewise improves the heat and light stability.

Suitable metal compounds known as stabilizers are in this context calcium, barium, strontium, zinc, cadmium, magnesium, aluminum and lead soaps of aliphatic carboxylic acids or hydroxy-carboxylic acids having of from about 12 to 32 carbon atoms, salts of said metals with aromatic carboxylic acids, for example benzoates or salicylates as well as (alkyl) phenolates of these metals, moreover organo-tin compounds, for example dialkyltin-thioglycolates and carboxylates.

Known epoxy stabilizers are, for example epoxidized higher fatty acids, for example epoxidized soy bean oil, tall oil, lin seed oil or epoxidized butyloleate as well as epoxides of long chain $\alpha$-olefins.

Suitable phosphites are trisnonylphenyl phosphite, trislauryl phosphite or esters of pentaerythritol phosphite.

Examples of suitable polyhydric alcohols are pentaerythritol, trimethylol-propane, sorbitol or mannitol, i.e. preferably alcohols having of from 5 to 6 carbon atoms and of from 3 to 6 OH groups.

A suitable stabilizer combination for halogen-free polyolefins, for example high, medium and low density polymers of $C_2$-$C_4$ $\alpha$-olefins, especially polyethylene and polypropylene or for copolymers of such $\alpha$-olefins comprises, calculated on 100 parts by weight of polymer, for example of from 0.01 to 5 parts by weight of one of the compounds to be used according to the invention, of from 0.05 to 5 parts by weight of a phenolic stabilizer, optionally of from 0.01 to 5 parts by weight of a sulfur-containing costabilizer, as well as optionally of from 0.01 to 3 parts by weight of a basic or neutral metal soap, for example calcium or zinc stearate, as well as optionally of from 0.01 to 5 parts by weight of a phosphite and optionally of from 0.01 to 5 parts by weight of a known UV stabilizer selected from the group consisting of the alkoxyhydroxybenzophenones, hydroxyphenylbenzotriazoles, salicyclic acid phenol esters, benzoic acid hydroxyphenol esters, benzylidene malonic acid mononitrile esters, the so-called quenchers such as nickel chelates or hexamethylphosphoric acid triamide.

A stabilizer combination suitable for the stabilization of halogen-containing polymers comprises, calculated on 100 parts by weight of polymer, for example of from 0.01 to 10 parts by weight of metal compounds known as stabilizers, of from 0.1 to 10 parts by weight of a known epoxy stabilizer, of from 0.05 to 10 parts by weight of a phosphite, of from 0.1 to 10 parts by weight of a polyhydric alcohol and of from 0.1 to 5 parts by weight of one of the compounds to be used according to the invention.

The following examples illustrate the invention:

EXAMPLE 1

2-Isopropyl-7,7,9,9-tetramethyl-1-oxa-3,8-diaza-4-oxo-spiro-[4,5]-decane

To 23.6 g of 2,2,6,6-tetramethyl-4-hydroxy-4-carbamoylpiperidinium chloride and 23 g of butyraldehyde in 100 g of glacial acetic acid there are added dropwise by stirring 19.6 g of concentrated sulfuric acid and stirring is continued for 20 hours at room temperature. Thereafter the mixture is concentrated in vacuo. The product obtained is taken up by a small quantity of ether/ethanol in a ratio of 1:1 and the solid matter obtained is suction-filtered. This matter is the sulfate of the desired compound. It is dissolved in a small quantity of water. The base is precipitated with ammonia. It is suction-filtered and recrystallized from alcohol. White crystals having a melting point ($M_p$) of from 150° C. to 151° C. are obtained in a nearly quantitative yield.

analysis of $C_{14}H_{26}N_2O_2$ (molecular weight 254): calculated: C, 66,1%; H, 10,3%; N, 11,0%. found: C, 65,9%; H, 10,5%; N, 10,6%.

EXAMPLES 2 to 14

The following compounds are synthesized as described in Example 1 from each time 23.6 of 2,2,6,6-tetramethyl-4-hydroxy-4-carbamoylpiperidinium chloride and a number of aldehydes. They are obtained as white crystals. Further details concerning the preparation and the analysis data can be seen from tables 1 and 2.

| Example No. | Compound |
|---|---|
| 2 | 2-butyl-7,7,9,9-tetramethyl-1-oxa-3,8-diaza-4-oxo-spiro-[4,5]-decane |
| 3 | 2-iso-butyl-7,7,9,9-tetramethyl-1-oxa-3,8-diaza-4-oxo-spiro-[4,5]-decane |
| 4 | 2-pentyl-7,7,9,9-tetramethyl-1-oxa-3,8-diaza-4-oxo-spiro-[4,5]-decane |
| 5 | 2-iso-pentyl-7,7,9,9-tetramethyl-1-oxa-3,8-diaza-4-oxo-spiro-[4,5]-decane |
| 6 | 2-hexyl-7,7,9,9-tetramethyl-1-oxa-3,8-diaza-4-oxo-spiro-[4,5]-decane |
| 7 | 2-heptyl-7,7,9,9-tetramethyl-1-oxa-3,8-diaza-4-oxo-spiro-[4,5]-decane |
| 8 | 2-iso-heptyl-7,7,9,9-tetramethyl-1-oxa-3,8-diaza-4-oxo-spiro-[4,5]-decane |
| 9 | 2-iso-octyl-7,7,9,9-tetramethyl-1-oxa-3,8-diaza-4-oxo-spiro-[4,5]-decane |
| 10 | 2-nonyl-7,7,9,9-tetramethyl-1-oxa-3,8-diaza-4-oxo-spiro-[4,5]-decane |
| 11 | 2-iso-nonyl-7,7,9,9-tetramethyl-1-oxa-3,8-diaza-4-oxo-spiro-[4,5]-decane |
| 12 | 2-undecyl-7,7,9,9-tetramethyl-1-oxa-3,8-diaza-4-oxo-spiro-[4,5]-decane |
| 13 | 2-phenyl-7,7,9,9-tetramethyl-1-oxa-3,8-diaza-4-oxo-spiro-[4,5]-decane |
| 14 | 2-(4-chloro-phenyl)-7,7,9,9-tetramethyl-1-oxa-3,8-diaza-4-oxo-spiro-[4,5]-decane |

Table 1

| Example No. | aldehyde quantity (g) | product crystallizes from | Mp. ° C |
|---|---|---|---|
| 2 | valer- 25 | acetone/$H_2O$ | 158–159 |
| 3 | i-valer- 25 | acetone | 189–190 |
| 4 | capro- 30 | ethanol/$H_2O$ | 122–123 |
| 5 | 2-ethyl-butyr- 30 | ethanol/$H_2O$ | 171–173 |
| 6 | enanth- 35 | ethanol/$H_2O$ | 141–142 |
| 7 | capryl- 30 | acetone | 130–132 |
| 8 | 2-ethyl-capron- 38 | ethanol | 137 |
| 9 | isononyl- 43 | ethanol/$H_2O$ | 162 |
| 10 | capric- 30 | acetone | 124–125 |
| 11 | isodecyl- 47 | ethanol | 155 |
| 12 | lauric- 40 | ethanol/$H_2O$ | 107 |
| 13 | benz- 32 | methanol | 250 |
| 14 | p-chlorbenz- 42 | methanol | 248–250 |

Table 2

| Example No. | formula molar weight | calc. C found. | calc. H found. | calc. N found. |
|---|---|---|---|---|
| 2 | $C_{15}H_{28}N_2O_2$ 268 | 67.1 66.7 | 10.5 10.7 | 10.5 10.6 |
| 3 | $C_{15}H_{28}N_2O_2$ 268 | 67.1 66.7 | 10.5 10.7 | 10.5 10.3 |
| 4 | $C_{16}H_{30}N_2O_2$ 282 | 68.0 69.0 | 10.7 11.7 | 9.9 9.1 |
| 5 | $C_{16}H_{30}N_2O_2$ 282 | 68.0 68.0 | 10.7 11.3 | 9.9 9.8 |
| 6 | $C_{17}H_{32}N_2O_2$ 296 | 69.0 69.0 | 10.8 11.1 | 9.5 9.6 |
| 7 | $C_{18}H_{34}N_2O_2$ 310 | 69.7 69.7 | 11.0 11.2 | 9.0 8.8 |
| 8 | $C_{18}H_{34}N_2O_2$ 310 | 69.7 69.0 | 11.0 11.2 | 9.0 9.4 |
| 9 | $C_{19}H_{36}N_2O_2$ 324 | 70.4 70.8 | 11.1 11.0 | 8.6 8.5 |
| 10 | $C_{20}H_{38}N_2O_2$ 338 | 71.0 70.7 | 11.2 11.4 | 8.2 7.9 |
| 11 | $C_{20}H_{38}N_2O_2$ 338 | 71.0 71.6 | 11.2 11.5 | 8.2 7.8 |
| 12 | $C_{22}H_{42}N_2O_2$ 366 | 72.2 72.9 | 11.5 11.9 | 7.7 7.4 |
| 13 | $C_{17}H_{24}N_2O_2$ 288 | 70.8 70.1 | 8.3 8.2 | 9.7 9.8 |
| 14 | $C_{17}H_{23}ClN_2O_2$ 322.5 | 63.3 63.4 | 7.1 7.0 | 8.7 9.0 |

EXAMPLE 15

2,2,7,7,9,9-hexamethyl-1-oxa-3,8-diaza-4-oxo-spiro-[4,5]-decane

To 23.6 g of 2,2,6,6-tetramethyl-4-hydroxy-4-carbamoylpiperidinium chloride and 20 g of acetone in 100 g of glacial acetic acid there are added dropwise while stirring 19.6 g of concentrated sulfuric acid and stirring is continued for 72 hours at a temperature of from 40° C. to 50° C. (at a reaction temperature of 80° C. the reaction time was reduced to 16 hours). After some time a clear solution formed, from which a precipitate separates in the course of the reaction, which is taken up in a small quantity of water after having been suction-filtered and is treated with ammonia or 50% sodium hydroxide solution. The desired compound thereby precipitates as a white compound, which may be recrystallized from ethanol after suction-filtering. Melting point from 236° C. to 237° C.

analysis for $C_{13}H_{24}N_2O_2$ (molecular weight 240): calculated: C, 65.0%; H, 10.0%; N, 11.7%. found: C, 65.2%; H, 10.4%; N, 11.4%.

EXAMPLES 16 to 32

As described in Example 15, the following compounds were synthesized in the form of white crystals from each time 23.6 g of 2,2,6,6-tetramethyl-4-hydroxy-4-carbamoylpiperidinium chloride and a number of ketones. Further details concerning the preparation and the analysis can be seen in Tables 3 and 4.

| Example No. | Compound |
|---|---|
| 16 | 2-ethyl-2,7,7,9,9-pentamethyl-1-oxa-3,8-diaza-4-oxo-spiro-[4,5]-decane |
| 17 | 2-propyl-2,7,7,9,9-pentamethyl-1-oxa-3,8-diaza-4-spiro-[4,5]-decane |
| 18 | 2-isopropyl-2,7,7,9,9-pentamethyl-1-oxa-3,8 diaza-4-oxo-spiro-[4,5]-decane |
| 19 | 2-butyl-2,7,7,9,9-pentamethyl-1-oxa-3,8-diaza-4-oxo-spiro-[4,5]-decane |
| 20 | 2-isobutyl-2,7,7,9,9-pentamethyl-1-oxa-3,8-diaza-4-oxo-spiro-[−4,5]-decane |
| 21 | 2-pentyl-2,7,7,9,9-pentamethyl-1-oxa-3,8-diaza-4-oxo-spiro-[4,5]-decane |
| 22 | 2-hexyl-2,7,7,9,9-pentamethyl-1-oxa-3,8-diaza-4-oxo-spiro-[4,5]-decane |
| 23 | 2-nonyl-2,7,7,9,9-pentamethyl-1-oxa-3,8-diaza-4-oxo-spiro-[4,5]-decane |
| 24 | 2,2-diethyl-7,7,9,9-tetramethyl-1-oxa-3,8-diaza-4-oxo-spiro-[4,5]-decane |
| 25 | 2,2-dipropyl-7,7,9,9-tetramethyl-1-oxa-3,8-diaza-4-oxo-spiro-[4,5]-decane |
| 26 | 2,2-dibutyl-7,7,9,9-tetramethyl-1-oxa-3,8-diaza-4-oxo-spiro-[4,5]-decane |
| 27 | 2-ethyl-2-pentyl-7,7,9,9-tetramethyl-1-oxa-3,8-diaza-4-oxo-spiro-[4,5]-decane |
| 28 | 2,2-dibenzyl-7,7,9,9-tetramethyl-1-oxa-3,8-diaza-4-oxo-spiro-[4,5]-decane |
| 29 | 2,2,4,4-tetramethyl-7-oxa-3,12-diaza-14-oxo-dispiro-[5,1,4,2]-tetradecane |
| 30 | 2,2,4,4-tetramethyl-7-oxa-3,14-diaza-15-oxo-dispiro-[5,5,5,2]-pentadecane |
| 31 | 2,2,4,4-tetramethyl-7-oxa-3,20-diaza-21-oxo-dispiro-[5,1,11,2]-heneicosane |
| 32 | 2,2,4,4,10,10,12,12-octamethyl-7-oxa-3,11,14-triaza-15-oxo-dispiro-[5,1,5,2]-pentadecane |

Table 3

| Example No. | ketone quantity (g) | crystallizes from | Mp. ° C |
|---|---|---|---|
| 16 | methyl-ethyl- 15 | ethanol/$H_2O$ | 202 |
| 17 | methyl-propyl- 25 | ethanol/$H_2O$ | 184 |
| 18 | methyl-i-propyl- 25 | ethanol/$H_2O$ | 171–173 |
| 19 | hexanone-2 30 | heptane-methanol | 172 |
| 20 | methyl-i-butyl- 30 | ethanol/$H_2O$ | 163 |
| 21 | heptanone-2 34 | acetone/$H_2O$ | 172 |
| 22 | octanone-2 34 | acetone/$H_2O$ | 140 |
| 23 | undecanone-2 51 | ethanol/$H_2O$ | 116 |
| 24 | diethyl- 26 | ethanol/$H_2O$ | 177 |
| 25 | heptanone-4 35 | ethanol/$H_2O$ | 200 |
| 26 | nonanone-5 42 | acetone | 159 |
| 27 | octanone-3 38 | acetone | 132 |
| 28 | dibenzyl- 40 | ethanol | 240–242 |
| 29 | cyclopentanone 26 | ethanol/$H_2O$ | 233–236 |
| 30 | cyclohexanone 30 | ethanol/$H_2O$ | 230–233 |
| 31 | cyclododecanone 36 | ethanol | 221 |
| 32 | triacetonamine 35 | acetone | 205–207 |

Table

| Example No. | formula molar weight | calc. C found | calc. H found | calc. N found |
|---|---|---|---|---|
| 16 | $C_{14}H_{26}N_2O_2$ 254 | 66.2 65.8 | 10.3 10.4 | 11.0 11.0 |
| 17 | $C_{15}H_{28}N_2O_2$ 268 | 67.2 67.3 | 10.5 10.8 | 10.5 10.5 |
| 18 | $C_{15}H_{28}N_2O_2$ 268 | 67.2 67.1 | 10.5 10.9 | 10.5 10.4 |
| 19 | $C_{16}H_{30}N_2O_2$ 282 | 68.1 68.4 | 10.7 11.0 | 9.9 9.9 |
| 20 | $C_{16}H_{30}N_2O_2$ 282 | 68.1 67.8 | 10.7 11.2 | 9.9 9.7 |
| 21 | $C_{17}H_{32}N_2O_2$ 296 | 69.0 69.0 | 10.8 11.0 | 9.5 9.5 |
| 22 | $C_{18}H_{34}N_2O_2$ 310 | 69.6 69.6 | 11.0 11.2 | 8.9 8.5 |
| 23 | $C_{21}H_{40}N_2O_2$ 352 | 71.6 71.7 | 11.4 11.7 | 8.0 8.0 |
| 24 | $C_{15}H_{28}N_2O_2$ | 67.2 | 10.5 | 10.5 |

Table-continued

| Example No. | formula molar weight | calc. C found | calc. H found | calc. N found |
|---|---|---|---|---|
| 25 | $C_{17}H_{32}N_2O_2$ 268 | 67.3 69.0 | 10.8 10.8 | 10.5 9.5 |
| 26 | $C_{19}H_{36}N_2O_2$ 296 | 68.9 70.3 | 11.2 11.1 | 9.5 8.7 |
| 27 | $C_{18}H_{34}N_2O_2$ 324 | 70.3 69.6 | 11.4 11.0 | 8.7 9.0 |
| 28 | $C_{25}H_{32}N_2O_2$ 310 | 69.1 76.6 | 11.2 8.2 | 8.8 7.2 |
| 29 | $C_{15}H_{28}N_2O_2$ 392 | 76.5 67.7 | 8.3 9.8 | 7.1 10.5 |
| 30 | $C_{16}H_{28}N_2O_2$ 266 | 67.7 68.6 | 10.1 10.0 | 10.5 10.0 |
| 31 | $C_{22}H_{40}N_2O_2$ 280 | 68.6 72.5 | 10.4 11.0 | 10.0 7.7 |
| 32 | $C_{19}H_{35}N_3O_2$ 364 | 72.1 67.7 | 11.2 10.4 | 7.4 12.5 |
|  | 337 | 67.5 | 10.5 | 12.1 |

EXAMPLE 33

2-ethyl-2,7,7,9,9-pentamethyl-1-oxa-3,8-diaza-4-oxo-8-oxyl-spiro-[4,5]-decane 0.1 g of sodium tungstate, 0.1 g of ethylene diamine-tetraacetic acid, and 6 ml of 30% hydrogen peroxide are added to 3 g of the product obtained in Example 16 in 20 ml of methanol. After standing for 120 hours, at 20° C, the mixture is concentrated in vacuo, suspended in 10 ml of water and suction-filtered. After drying it is recrystallized from n-heptane/acetone and 2.0 g of orange colored crystals are obtained having a melting point of from 154° to 156° C.

analysis data for $C_{14}H_{25}N_2O_3$ (molecular weight 269): calculated: C, 62.4%; H, 9.3%; N, 10.4%. found: C, 62.5%; H, 9.6%; N, 10.4%.

EXAMPLE 34 p-tert-butylbenzoate of 2,2-diethyl-7,7,9,9-tetramethyl-1-oxa-3,8-diaza-4-oxo-spiro-[4,5]-decane 2.7 g of the compound obtained in Example 24 and 1.8 g of p-tert-butylbenzoic acid are refluxed with 50 ml of ethanol for 10 minutes. After cooling the precipitated white crystals are suction-filtered and dried. Melting point of from 242° to 245° C.

EXAMPLE 35

This example demonstrates the light-stabilizing action of some of the compounds according to the invention used in a poly-α-olefin.

100 parts by weight of polypropylene having a melt index i₅ of about 6 g/10 minutes (determined according to ASTM D 1238-62 T) and a density of 0.96 g/cm³ are mixed with 0.1 part by weight of a bis-(4'-hydroxy-3'-tert-butyl-phenol)butanoic acid ester 0.15 parts by weight of laurinethiopropionic acid ester 0.2 parts by weight of calcium stearate and 0.3 parts by weight of the stabilizer according to the invention to be examined and the mixture is homogenized on a two roller mill at 200° C for 5 minutes. The molten plastics composition is rolled at 200° C to give a plate having a thickness of 1 mm. Test specimens are punched from the cooled plate according to DIN (German industrial standard) 53 455. Comparative test specimens are prepared in an analogous manner, but without the use of the stabilizer to be examined.

For determining the light stability, the specimens are exposed to radiations of varying intensity in a weather-ometer (Xenotest 150$^R$) of Messrs. Original Hanau Quarzlampen GmbH. The intensity of radiation is moduled by 6 IR windows and 1 UV window (according to DIN 53387). The time of exposure in hours is measured after which the absolute elongation at break has dropped to 10%. The elongation at break is determined on a tension test machine of Messrs. Instron at a draw off rate of 5 cm/minute.

The following table shows the results obtained:

| Stabilizer according to the invention of example | time of exposure (hours) |
|---|---|
| 2 | >800 |
| 5 | >800 |
| 12 | >800 |
| 18 | >800 |
| 23 | >800 |
| 28 | >800 |
| 30 | >800 |
| without stabilizer (comparative test) | 560 |

What is claimed is:
1. A compound of the formula

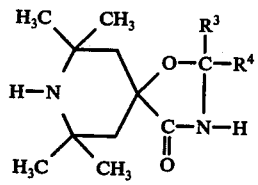

wherein $R^3$ and $R^4$ each are identical or different substituents selected from the group consisting of hydrogen, alkyl- or isoalkyl of from 1–30 carbons, aryl of 6 or 10 carbons, unsubstituted or substituted by halogen or alkyl of 1–4 carbons, phenylalkyl of 7–10 carbons, or $R^3$ and $R^4$ are, together with the attached carbon, cycloalkyl of 4–15 carbons, unsubstituted or substituted by $C_1 - C_4$ alkyl, or a group of the formula

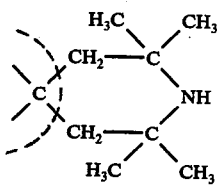

2. A compound of claim 1, wherein $R^3$ is hydrogen, $R^4$ is isopropyl, butyl, isobutyl, pentyl, isopentyl, hexyl, heptyl, isoheptyl, nonyl, isononyl, undecyl, phenyl or p-chlorophenyl.

3. A compound of claim 1, wherein $R^3$ is methyl and $R^4$ is ethyl, propyl, isopropyl, butyl, isobutyl, pentyl, hexyl, or nonyl.

4. A compound of claim 1, wherein $R^3$ is ethyl and $R^4$ is n-pentyl.

5. A compound of claim 1, wherein $R^3$ and $R^4$ are identical and are methyl, ethyl, propyl, butyl or benzyl.

6. A compound of claim 1, wherein $R^3$ and $R^4$ are, together with the attached carbon, a cyclopentyl, cyclohexyl or cyclododecyl ring or a group of the formula

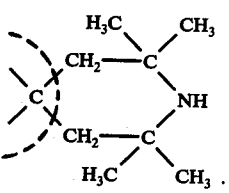

* * * * *